US005190200A

United States Patent [19]

Hammerlund

[11] Patent Number: 5,190,200

[45] Date of Patent: Mar. 2, 1993

[54] BIODEGRADABLE DENTAL FLOSS CONTAINER

[75] Inventor: Gary M. Hammerlund, Grand Rapids, Mich.

[73] Assignee: Ranir/DCP Corporation, Grand Rapids, Mich.

[21] Appl. No.: 813,199

[22] Filed: Dec. 23, 1991

[51] Int. Cl.⁵ .............................. B26F 3/00; B65D 5/00
[52] U.S. Cl. ........................................ 225/42; 225/50; 225/77; 229/124; 229/149
[58] Field of Search ............... 225/42, 48, 106, 77, 225/50, 90; 229/124, 149; 206/806, 44 R; 132/323, 324, 325

[56] References Cited

U.S. PATENT DOCUMENTS

| | | | |
|---|---|---|---|
| 1,433,439 | 10/1922 | Weis | 229/149 |
| 2,290,359 | 7/1942 | Ringler | 229/149 X |
| 4,262,816 | 4/1981 | Margulies | 225/106 X |
| 4,308,986 | 1/1982 | Parrilli | 206/806 X |
| 4,315,569 | 2/1982 | Jaeschke | 206/806 X |
| 4,925,073 | 5/1990 | Tarrson et al. | 225/77 X |

Primary Examiner—Frank T. Yost
Assistant Examiner—Clark F. Dexter
Attorney, Agent, or Firm—Price, Heneveld, Cooper, Dewitt & Litton

[57] ABSTRACT

An integral recyclable dental floss package/container/dispenser, and a blank therefor, having an integral structure of one-piece, biodegradable material, preferably paperboard, there being a hang tab integral with extending upwardly from, and separable from, the back panel. The top closure has an inner panel extending rearwardly from the fornt panel, having a floss dispensing orifice and cutter, and an outer top cover panel extending forwardly from the rear wall.

17 Claims, 3 Drawing Sheets

BIODEGRADABLE DENTAL FLOSS CONTAINER

BACKGROUND OF THE INVENTION

This invention relates to a dental floss package/container/dispenser.

For some years, dental floss has been marketed in molded, polymeric containers which have a floss outlet orifice and a floss cutter element, to also serve as a floss dispenser, for periodic, e.g., daily, dispensing and cutting of selected lengths of floss by the user. Marketing of these containers of dental floss typically involves encompassing the polymeric container in a blister pack on a hang card. The purchaser then cuts the transparent polymeric blister from the card to release the floss container for use. The polymeric blister and the polymer coated paperboard hang card are then discarded as trash. Unfortunately, neither the polymeric blister nor the polymeric coated paperboard hang card is biodegradable. When the floss in the plastic container is later all used, the container is also discarded as trash. This container is not biodegradable either. Hence, although these items are individually relatively small, the millions of such polymeric blisters, polymer coated hang cards, and polymeric containers used each year create a substantial amount of nonbiodegradable trash to be incinerated or buried in a landfill.

SUMMARY OF THE INVENTION

An object of this invention is to provide a unique dental floss package/container/dispenser which serves to hold and display the product in a store without blister packaging being required, subsequently serves to dispense the floss until the floss in the container is all used, and which is biodegradable when disposed of after use, so as not to clutter the environment for an extended time period.

Another object of this invention is to provide an integral, biodegradable, paperboard dental floss package/container/dispenser which has a hang tab integral therewith, but readily removable therefrom after purchase.

The novel dental floss container is of paperboard. It has a hang tab of the same material and integral with the rear wall of the container along a perforated juncture, for later ready separation of the container from the hang tab after purchase thereof. The top closure of the container comprises a top inner panel having a floss outlet orifice and a floss cutter, with a creased juncture connection to the front wall to fold over the top of the container, and a top, outer, cover panel having a creased juncture to the rear panel, to fold over the top of the container and over the top inner panel with a tab to slip into a slot in the front panel for closure retention. Therefore, the same structure is used for packaging, display prior to purchase, containment of the product after purchase, dispensing of the floss after purchase, and ultimately is entirely biodegradable for optimum disposal.

Another object of this invention is to provide a blank for forming a novel biodegradable dental floss package/container/dispenser. The blank is an integral structure of interconnected front, side and rear panels, as well as a top inner cover panel extending from the front panel upper edge, and a top outer cover panel extending from the top edge of the front panel.

These and other objects, advantages and features of the invention will become apparent upon studying the following detailed specification in conjunction with the drawings.

DESCRIPTION OF THE PREFERRED EMBODIMENTS

Figure 1:
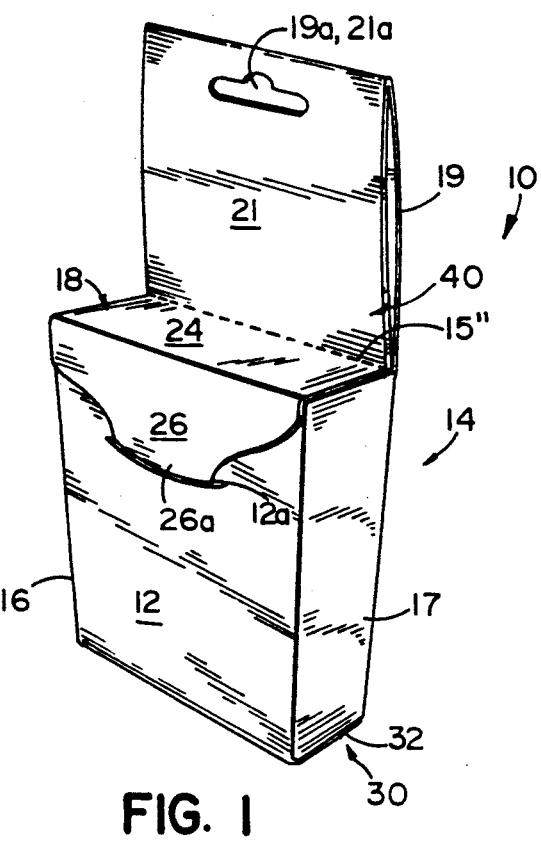
FIG. 1 is a perspective view of the novel dental floss package/container/dispenser.
Figure 2:
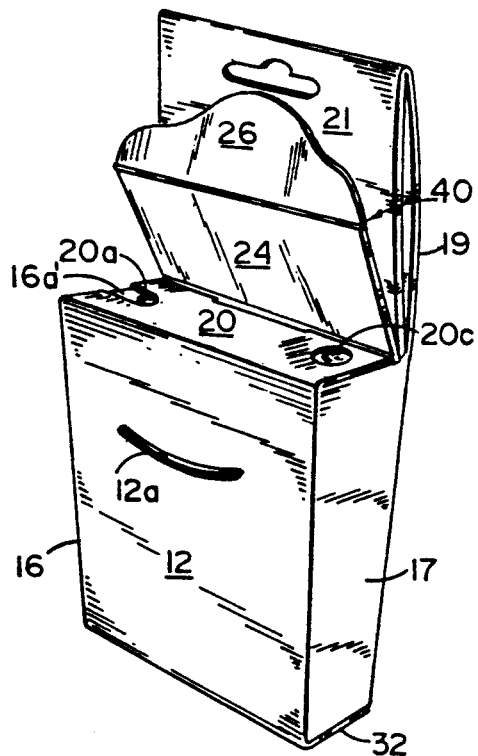
FIG. 2 is a perspective view of the package/container/dispenser in FIG. 1, showing the top cover panel and flap in the open condition.
Figure 3:
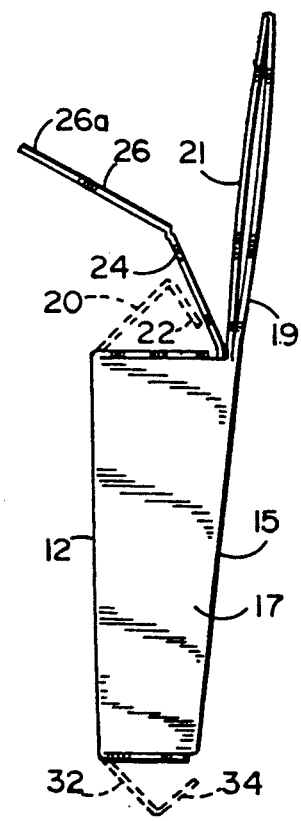
FIG. 3 is a side elevational view of the package/container/dispenser in FIGS. 1 and 2, showing the top cover panel and flap in open condition, and showing, in phantom lines, the top inner panel and flap open and the bottom panel and flap open.

Referring now particularly to FIGS. 1-4, the total dental floss package/container/dispenser 10 is an integral structure of recyclable material, normally a cellulosic material such as paperboard. The structure is preferably formed of the blank 100 in FIG. 4, although the bottom closure can vary such as is shown, for example, by the equivalent bottom closures in FIGS. 5-9, forming part of blanks 100a, 100b, 100c, 100d and 100e. For convenience, therefore, the structure will be described relative to the blank 100.

Structure 10 includes a front wall 12, a rear wall 14, a pair of side walls 16 and 17, a top closure subassembly 18, a bottom closure subassembly 30, and a hang tab 40, all of these components being of an integral assembly.

Figure 4:
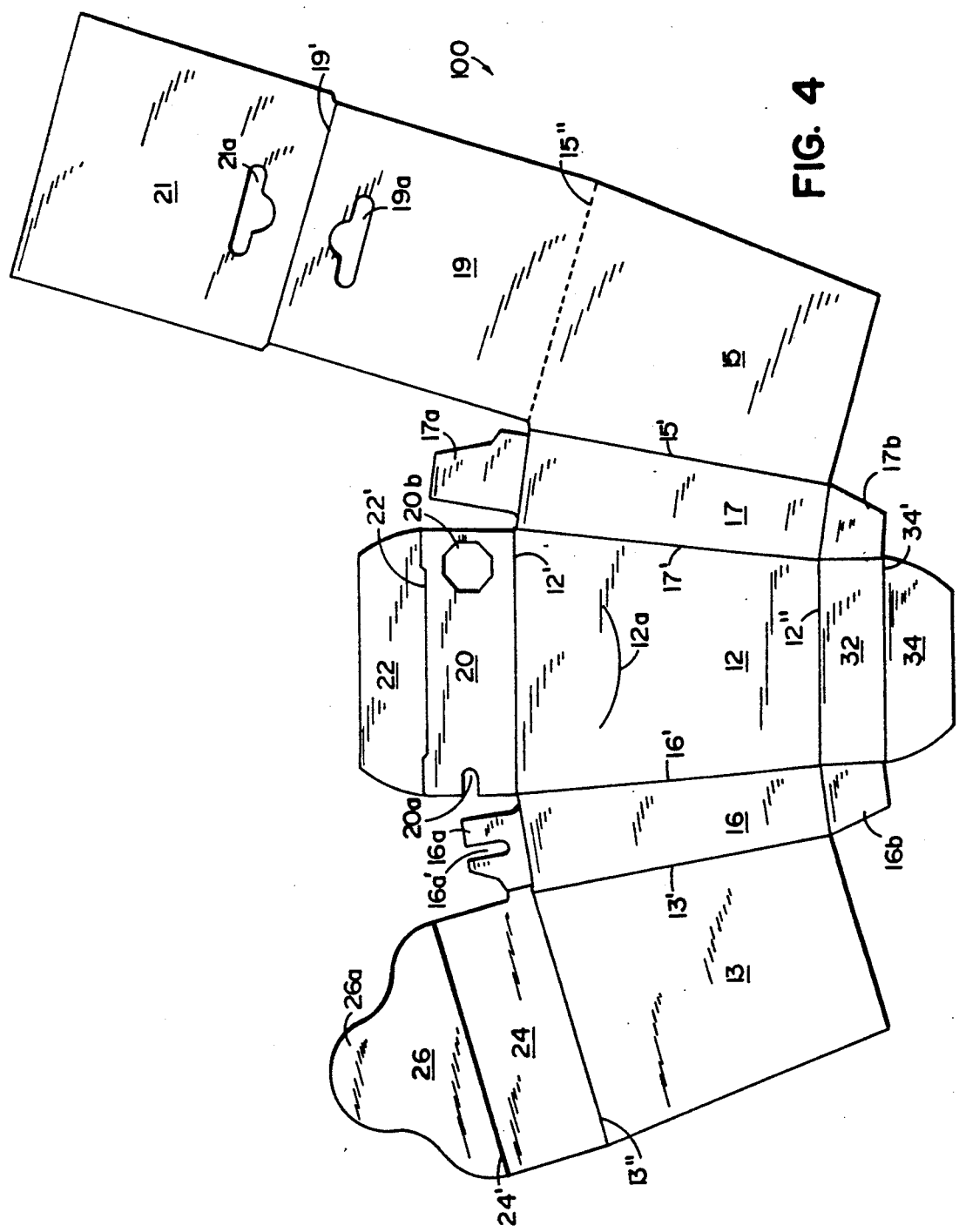
FIG. 4 is a plan view of a blank for the structure in FIGS. 1-3.
Figure 5:
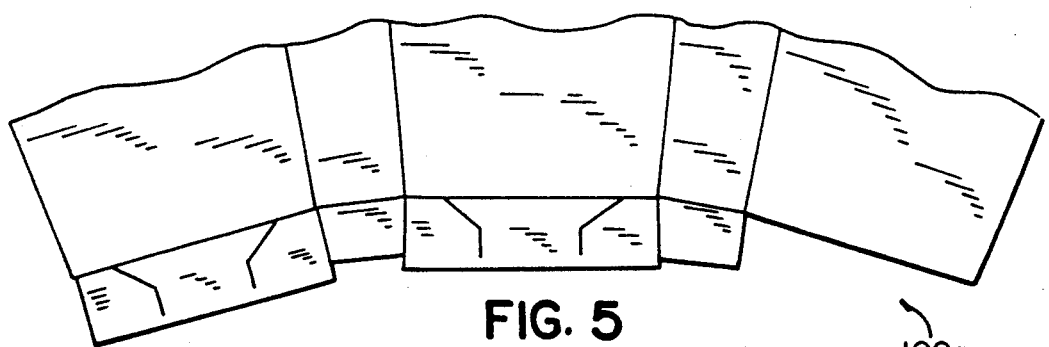
FIG. 5 is a fragmentary plan view of an alternate blank showing a second embodiment of the bottom closure
Figure 6:
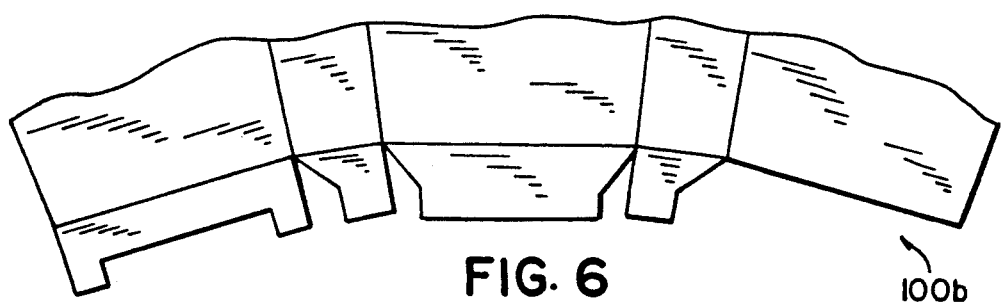
FIG. 6 is a fragmentary plan view of a third embodiment of the bottom closure.
Figure 7:
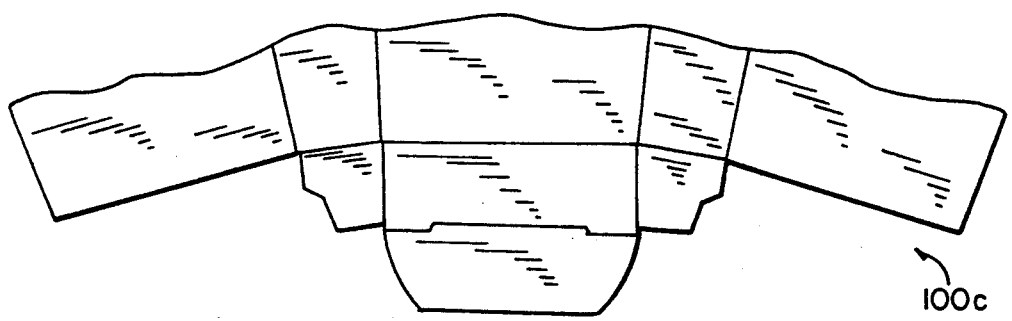
FIG. 7 is a fragmentary plan view of a fourth embodiment of the bottom flap.
Figure 8:
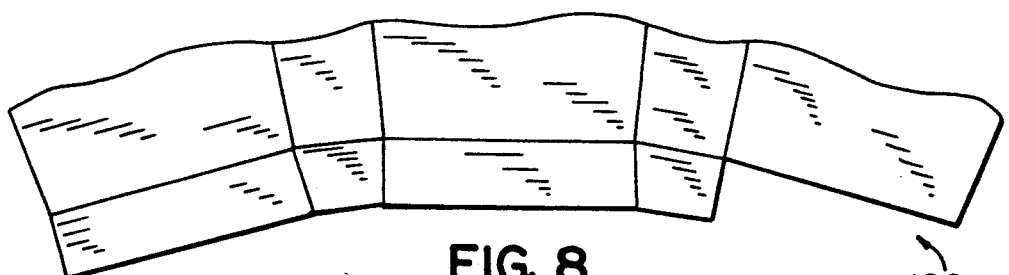
FIG. 8 is a fragmentary plan view of a fifth embodiment of the bottom closure.
Figure 9:
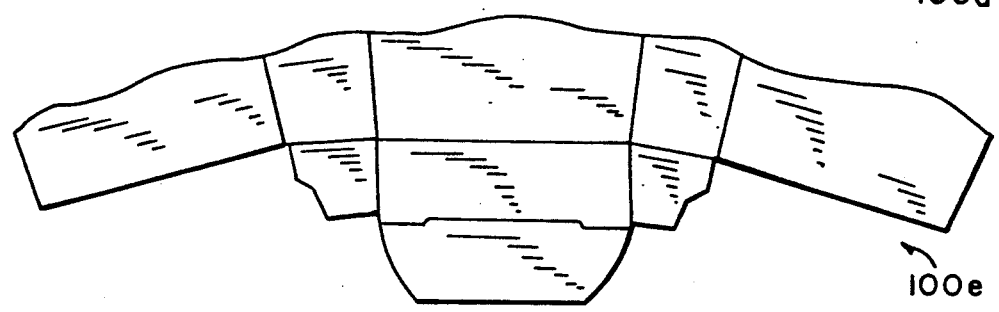
FIG. 9 is a fragmentary plan view of a sixth embodiment of the bottom closure.

Front wall 12 is preferably a simple trapezoid, but may alternatively be a rectangle, having an upper edge 12' and a lower edge 12''. Extending integrally from upper edge 12' is a top inner panel 20, with a creased joint at 12' between panel 20 and panel 12, and a flap 22 joined to panel 20 with a creased joint at 22'. The depth of panel 20 is substantially equal to the depth of the package, while the width of panel 20 is substantially equal to the width of the package. In top inner panel 20, and preferably at one end thereof such as the left end shown in FIG. 4, is a floss outlet orifice 20a. In the opposite end is a pocket orifice 20b for receiving a conventional floss cutter 20c (FIG. 2) as of thin metal. This top inner panel and flap, as well as the top cover panel, flap and tab to be described hereinafter, comprise the top closure subassembly 18.

Extending downwardly from the lower edge 12'' of front panel 12 is a bottom closure panel 32 joined to panel 12 by a creased integral joint at 12''', and a flap 34 which is joined to panel 32 by an integral creased joint line 34'. The depth and width of panel 32 is substantially equal the depth and width of the bottom opening of the package. Integrally joined to front panel 12, and extending laterally thereof, is the pair of side panels 16 and 17 joined to front panel 12 by integral creased joint lines 16' and 17'. At the of panel 17 is a fold flap 17a, while extending from the lower edge of panel 17 is a second fold flap 17b. Extending downwardly from the lower edge of panel 16 is a lower flap 16b, while extending from upper edge of side panel 16 is an upper flap 16a which also includes an elongated slot orifice 16a' to coincide with orifice 20a of top panel 20 when the blank 100 in FIG. 4 is formed into the package/container/dispenser 10 in FIGS. 1-3.

Extending laterally from side panel 16 is a first rear panel 13 which forms part of the rear wall 14. It is joined to side panel 16 by an integral creased joint 13'. Extending upwardly from the upper edge 13" of panel 13 is top cover panel 24 which has a depth slightly greater than the depth of top inner panel 20, to fit over the outside of the package in a manner to be described hereinafter. Joined to top cover panel 24 at integral crease line 24' is flap 26 with a narrower tab 26a on the outer end thereof. Tab 26a is configurated and spaced relative to panel 24 and the upper edge 12' of front panel 12 to fit over the outside of the upper part of panel 12 and down through the arcuate slot 12a in front panel 12. Panel 13 is to overlap and be folded inside of the second back panel 15 which extends laterally from side panel 17 at creased joint line 15'.

Extending upwardly from the upper edge 15" of the second back panel 15 is a hang tab which preferably is formed to be of double thickness. Specifically, a first hang tab panel 19 is integrally joined at perforated joint 15" to the upper edge of panel 15, and has integrally joined to its upper edge 19' a second hang tab panel 21, so as to be foldable about crease joint 19' to coincide and be secured as by adhesive to panel 19. Orifices 19a and 21a are spaced an equal amount from edge 19' to coincide and thereby form a hanging orifice for suspension of the entire structure on a display hanger (not shown), typically a bar.

Manufacture of the novel product is preferably achieved by die cutting paperboard to the blank configuration depicted in FIG. 4. The paperboard is preferably coated with a biodegradable and recyclable water repellant varnish or the like. Prior to formation of the container by folding, a suitable metal or equivalent floss cutter 20c is crimped into the receiving pocket 20b in conventional fashion. The blank structure is then folded to create the novel package/container/dispenser of FIGS. 1-3 by folding side panels 16 and 17 about their crease lines 16' and 17' to be normal to front panel 12, folding inner back panel 13 ninety degrees about crease line 13' and outer back panel 15 ninety degrees about crease line 15' to overlap panel 13 and preferably be adhered thereto by a suitable adhesive. Inner hang tab panel 21 is folded downwardly about crease line 19' to overlap, engage and preferably be adhered to outer tab panel 19. Bottom flaps 17b and 16b are folded inwardly, as are bottom panel 32 and flap 34, to close the bottom of the container. After the spool of floss, preferably on a biodegradable spindle (not shown) is placed into the container, top edge flaps 17a and 16a are closed ninety degrees to be over the top opening, followed by closure of top inner panel 20 and its flap 22 to the position illustrated in FIG. 2. Then top outer cover panel 24 is folded over the inner panel 20 and over a portion of the upper front of front panel 12 while table 26a is slid down into slot 12a to retain the outer cover in closed condition.

The package/container/dispenser of dental floss is then ready to be shipped, displayed, sold and used, employing only this structure. More specifically, the item can be shipped as such without the need for blister packaging or the equivalent, displayed in the retail establishment by being suspended on a typical hanger utilizing the orifice in hang tab 40, and removed from the hanger at the time of purchase. The purchaser then separates the hang tab from the package by tearing along the perforated joint 15". This hang tab 40 is biodegradable so as to present no long term problem to the environment.

When it is desired to dispense some dental floss, the top outer cover 24 is lifted, floss is pulled out of the exit orifice, cut off at cutter 20c, and the package reclosed by placing tab 26a in slot 12a. When the floss is totally used up, the totally biodegradable container can be readily disposed of without long term damage to the environment.

The lower closure structures illustrated in FIGS. 5-9 at 100a-100e can be employed alternatively to that shown in FIG. 4. These are set forth as illustrative. Various additional structural changes could conceivably be made in the preferred embodiment set forth without departing from the inventive concept. Hence, it is intended that the invention is to be limited only by the scope of the appended claims and the reasonably equivalent structures to those defined therein, rather than by the specific details of the preferred embodiment set forth as illustrative of the invention.

The embodiments of the invention in which an exclusive property or privilege is claimed are defined as follows:

1. An integral, recyclable, dental floss package/container/dispenser of a three-dimensional structure of cellulosic material, comprising:
   a front wall panel having a top edge;
   a slit in said front wall panel;
   first and second side wall panels integrally joined to said front wall panel;
   a first rear wall panel;
   a second rear wall panel inwardly of, parallel to and overlapping said first rear wall panel;
   a bottom end wall;
   a top inner panel extendible between said front and rear panels over the top of said package, and having a floss exit orifice and a floss cutter;
   a top cover panel over said top inner panel;
   a top cover panel flap having a creased juncture with said top cover panel, and having a tab engageable with said slit to retain said top cover panel closed over said top inner panel;
   a hang tab integral with and extending upwardly from said first rear wall panel;
   said hang tab having an orifice for suspending said package/container/dispenser on a display hanger; and
   a perforated integral juncture between said hang tab and said first rear wall panel for ultimate separation of said hang tab from said package/container/dispenser by a consumer.

2. The dental floss dispensing package/container/dispenser of claim 1 wherein said rear wall comprises inner and outer laterally overlapping panels adhered together.

3. The dental floss dispensing package of claim 1 wherein said hang tab comprises first and second panels secured together.

4. The dental floss dispensing package of claim 1 wherein said top inner panel has a creased juncture with said front panel and is folded toward said rear wall over the top of the package, and said top cover panel has a creased juncture with said rear panel and is folded toward said front panel, over said top inner panel.

5. An integral, one-piece, cellulosic, recyclable, dental floss package/container/dispenser, comprising:
   a one-piece paperboard element defining a rear wall, a front wall, a pair of side walls, a top inner panel having a floss exit orifice and a floss cutter, a top closure and a bottom closure; and
   an integral hang tab extending upwardly above said top closure for suspending said dental floss package and dental floss therein from a display hanger.

6. The dental floss dispensing package/container/dispenser of claim 5 wherein said hang tab is integral with and extends upwardly from said rear wall, and is joined to said rear wall by a releasable joint to be readily separable from said rear wall.

7. The dental floss dispensing package/container/dispenser of claim 6 wherein said releasable joint comprises a perforated integral juncture between said hang tab and said rear wall for separation of said hang tab from said package/container/dispenser.

8. The dental floss dispensing package/container/dispenser of claim 7 wherein said hang tab has two panels folded together with one of said panels being integral with said rear wall.

9. The dental floss dispensing package/container/dispenser of claim 8 wherein said rear wall has two panels overlapping with and adhered to each other.

10. The dental floss dispensing package/container/dispenser of claim 6 wherein said hang tab has an orifice for receiving a suspension hanger.

11. The dental floss dispensing package/container/dispenser in claim 5 wherein said top closure comprises a top inner panel having a floss outlet and a top outer cover panel over said top inner panel.

12. The dental floss dispensing package/container/dispenser in claim 11 wherein said top inner panel is integral with said front wall and said top outer cover panel is integral with said rear wall.

13. A biodegradable, one-piece dental floss container, dispenser and display mount comprising:
   a single paperboard structure having spaced front and rear walls, a pair of spaced side walls joined to said front and rear walls, and top and bottom closures formed by panels joined to said front and rear walls;
   a hang tab integral with and extending upwardly from said rear wall, and having a perforated juncture with said rear wall for separation of said hang tab from said container; and
   a floss dispensing opening through a panel of said container and a floss cutter adjacent said opening.

14. A two-dimensional, biodegradable paperboard blank for forming a three-dimensional dental floss display, container, and dispenser comprising:
   a first back panel having a top edge and a bottom edge, and having an outer top cover panel and flap extending from said top edge of said first back panel by a creased fold joint;
   a first side panel extending laterally from said first back panel and joined thereto by a creased fold joint;
   a front panel having a top edge and a bottom edge, and extending laterally from said first side panel and joined thereto by a creased fold joint, said front panel having an inner top panel and flap extending from said top edge of said front panel;
   a second side panel extending laterally from said front panel and joined thereto by a creased fold joint;
   a second back panel having a top edge, and extending laterally from said second side panel and joined thereto by a creased fold joint;
   a hang tab integral with and extending from said top edge of said second back panel and separable from said second back panel;
   a bottom panel extending from said bottom edge of said front panel and said side panels; and
   a floss outlet orifice in said blank.

15. The blank of claim 14 wherein said hang tab is integrally joined to said second back panel by a perforated joint for ready separation of said hang tab.

16. The blank of claim 15 wherein said orifice is in said inner top panel.

17. The blank of claim 15 wherein said front panel includes a slit for receiving said outer top cover panel flap.

* * * * *

UNITED STATES PATENT AND TRADEMARK OFFICE
CERTIFICATE OF CORRECTION

PATENT NO. : 5,190,200
DATED : March 2, 1993
INVENTOR(S) : Gary M. Hammerlund

It is certified that error appears in the above-identified patent and that said Letters Patent is hereby corrected as shown below:

Title Page:
In the Abstract, line 7;
    "fornt" should be -- front --;

Column 3, line 3;
    After "at the" insert -- upper end --;

Column 5, line 5;
    "said rear panel" should be -- said second rear wall panel --;

Column 5, lines 38 & 39;
    After "comprises" delete -- a top inner panel having a floss outlet and --.

Signed and Sealed this

Twenty-sixth Day of April, 1994

Attest:

BRUCE LEHMAN

*Attesting Officer*      *Commissioner of Patents and Trademarks*